United States Patent [19]

Hadwiger

[11] Patent Number: 4,978,381

[45] Date of Patent: * Dec. 18, 1990

[54] METHOD FOR TREATING CEREAL CROP SEED WITH CHITOSAN TO ENHANCE YIELD, ROOT GROWTH, AND STEM STRENGTH

[75] Inventor: Lee A. Hadwiger, Pullman, Wash.

[73] Assignee: Washington State University Research Foundation, Pullman, Wash.

[*] Notice: The portion of the term of this patent subsequent to Sep. 12, 2006 has been disclaimed.

[21] Appl. No.: 344,287

[22] Filed: Apr. 4, 1989

Related U.S. Application Data

[63] Continuation-in-part of Ser. No. 795,702, Nov. 5, 1985, abandoned, which is a continuation of Ser. No. 658,084, Oct. 5, 1984, abandoned.

[51] Int. Cl.$^5$ .............................................. A01N 43/16
[52] U.S. Cl. .......................................... 71/77; 71/88; 47/57.6
[58] Field of Search ..................................... 71/88, 77

[56] References Cited

U.S. PATENT DOCUMENTS 4,812,159 3/1989 Freepons ................................. 71/16

OTHER PUBLICATIONS

Allan and Hadwiger, Exper. Mycol., 3, 1979, pp. 285–287, "The Fungicidal Effect of Chitosan on Fungi of Varying Cell Wall . . . ".

L. A. Hadwiger, "Chitosan, A Natural Regulator in Plant-Fungal Pathogen Interactions, Increases Crop Yields", Chitin, Chitosan and Related Enzymes, Academic Press Inc., 1984, (New York, N.Y.), pp. 291–302.

R. L. Rawls, "Prospects Brighten Converting Chitin Wastes to Valuable Products",—Chemical and Engineering New, 1984, (Washington, D.C.), vol. 62, pp. 42–45.

Wheat Res. Rev. for Washington Wheat Commission, Washington Assn. of Wheat Growers and State Dept. of Agriculture, 1983, (Pullman, Washington), pp. 27–28.

Research Grant Proposal, L. A. Hadwiger, "Evaluation of Chitosan as a Seed Treatment".

Wheat Research Review for Washington Wheat Commission, Washington Association of Wheat Growers and State Department of Agriculture, 1984, (Pullman, Washington), pp. 64–65.

Research Grant Proposal, L. A. Hadwiger, "Mode of Action of Chitosan in Reducing Disease-Caused Lodging of Winter Wheat".

Washington, Sea Grant Program, 1985, (Pullman, Washington), See Entire Document, Research Grant Proposal, L. A. Hadwiger, "Chitosan and Enhancedd Wheat Yield".

Wheat Res. Rev. for Washington Wheat Commission, Washington Assn. of Wheat Growers and State Dept. of Agriculture, 1981, (Pullman, Washington), pp. 63–64, Research Grant Proposal, L. A. Hadwiger, "Evaluation of Chitosan as a Systemic Fungicide".

*Primary Examiner*—Richard L. Raymond
*Assistant Examiner*—Eric J. Kraus
*Attorney, Agent, or Firm*—Wegner, Cantor, Mueller & Player

[57] ABSTRACT

Commerically produced chitosan applied to cereal crop seeds at rates of 60 μg to 1000 μg per gram of seed enhances root development, crown diameter, mature straw strength and crop yield. Dry chitosan, when dissolved in dilute acid and neutralized, is applied directly to cereal crop seed with only minor modification to seed treating machinery and methods. In addition to a clear benefit in cereal crop yield, the chitosan treated seed can be planted early to reduce erosion and it can be planted in regions having soil infested with root rotting organisms and not suffer extensive lodging that would prevent seed recovery by commercial harvesters.

12 Claims, No Drawings ic carbamate (Benlate), which reduce the incidence of root rotting and thus retain original straw strength. Extended use of this chemical, however, has resulted in the selection of fungal pathogens that are resistant to its fungicidal effect and, thus, effectiveness is greatly diminished. Only emergency Food and Drug Administration clearance has been obtained in the United States of America for use of this chemical on wheat because of potential side effects. Finally, its cost of treatment is very high.

METHOD FOR TREATING CEREAL CROP SEED WITH CHITOSAN TO ENHANCE YIELD, ROOT GROWTH, AND STEM STRENGTH

This application is a continuation-in-part of my U.S. application Ser. No. 795,702, filed Nov. 5, 1985, which was a continuation of my U.S. application Ser. No. 658,084, filed Oct. 5, 1984 and now both abandoned.

FIELD OF THE INVENTION

This invention pertains to methods for treating the seed of cereal crops, which are defined as members of the grass family (Graminae) that produce edible, starchy grains and are characterized by long, narrow blades. Wheat, barley, oats, rye, and rice are cereal crops.

BACKGROUND OF THE INVENTION

One of the major problems in growing cereal crops is the lodging (falling over) of plants prior to harvest, which prevents the mechanical recovery at harvest of high yielding plant heads. Researchers have tried to alleviate this problem by:
1. Breeding stiffer stemmed varieties;
2. Using chemical treatments such as benzamidazole-type fungicides (Benlate) to reduce root rot;
3. Recommending that planting dates for winter crops be delayed so that organisms have minimal time to initiate the root rotting process prior to the slow growth phase of winter; and
4. Recommending no-till or minimum tillage procedures that leave crop debris to reduce the erosion that is rampant when planting dates ar delayed.

Each of these alternative procedures are partial solutions to yield losses. However, each has serious drawbacks.

It has been impossible to breed for straw strength and still retain all of the other desirable agronomic traits, e.g., winter hardiness, milling quality yield, disease resistance, etc., at the same time because the high yielding heads place unusually severe strain on the plant stem.

Lodging has been reduced by fungicides that are derivatives of methyl 1-(butylcarbamoyl)-2-benzimidazole carbamate (Benlate), which reduce the incidence of root rotting and thus retain original straw strength. Extended use of this chemical, however, has resulted in the selection of fungal pathogens that are resistant to its fungicidal effect and, thus, effectiveness is greatly diminished. Only emergency Food and Drug Administration clearance has been obtained in the United States of America for use of this chemical on wheat because of potential side effects. Finally, its cost of treatment is very high.

Delaying the planting date has reduced lodging; however, it prevents the time dependent development of large seedling plants needed for ground cover prior to the onset of winter rains and erratic snow melts that erode away large tonnages of soil each year. The latter problem can be reduced by minimal tillage practices that leave straw on top of the soil at planting time. However, minimal tillage, which produces generally lower yields, leaves weeds untilled as well and must be accompanied by additional herbicide and pesticide treatments requiring expensive machinery for application.

Accordingly, a need exists for a method that will increase the straw strength and the root development of cereal crops at a commercially feasible cost while still maintaining or increasing the amount of yield.

SUMMARY OF THE INVENTION

This invention comprises a novel chitosan seed treatment that strengthens the stems of cereal crop plants, such as wheat, oats, barley, rye, and rice, helping to preserve their water-carrying capacity, greatly reducing lodging (plants falling over before harvest), and increasing yield. The lodging problem is most severe for winter crops when seed is planted early so that the plants can cover the ground prior to the soil eroding winter rains. Thus, by using this seed treatment, farmers will be able to plant crops early and reduce the erosion loss that exceeds 9071.8 kilograms per 0.4047 hectare in some parts of the United State of America.

While this invention is applicable to any of the cereal crops, primary work has been done with wheat, barley, and oats and this specification will discuss the invention using these cereal grains as an embodiment.

The problem of lodging of high yielding cereal plants can be rectified by seed treatment with the naturally occurring carbohydrate, chitosan. Commercially produced chitosan when applied in an aqueous form to cereal seeds is able, under field conditions, to greatly increase the development of the plant's root system, to substantially increase the diameter of the stem, and, in association with these specific and other intangible morphological and biochemical developments, to enhance yield. The chitosan treatment results in a plant that is beneficial to erosion control, resistant to lodging, and superior in yield over non-treated plants. The method of treatment comprises the direct application of chitosan derived from various shell sources, such as crab, lobster, shrimp and other marine life, in a nearly neutral aqueous solution to wheat seeds prior to planting.

Accordingly, it is a primary object of the present invention to provide a method for increasing the straw strength and root development of cereal crops while increasing the amount of yield.

This and further objects and advantages will be apparent to those skilled in the art in connection with the detailed description of the preferred embodiments set forth below.

DETAILED DESCRIPTION OF THE PREFERRED EMBODIMENTS

Chitosan is a polymer made up of a hexosamine sugar (glucosamine) whose molecules are linked (1, 4) into chains that can exceed molecular weights of one million. Chitosan compounds in a range of up to and exceeding $1 \times 10^6$ molecular weight are derived commercially from chitin. Chitin, an amino cellulose derivite, is the second most abundant polymer occurring in nature, existing, for example, in the cell walls of fungi, bovine cartilage, and the hard shells of insects and crustaceans. Wastes from the shrimp, lobster, and crab seafood industries contain 10-30% chitin. Chitosan is produced by deacetylating chitin. This invention is effective if the deacetylation exceeds about 90% and it is most effective when approaching 100% deacetylation.

Dry chitosan as either flakes, granules, or powder is suitable as a starting material. The more finely dispersed the chitosan, the more quickly it can be dissolved in a dilute aqueous acid (e.g., 1% acetic acid or dilute hydrochloric acid, sulfuric acid, or formic acid).

Typically, a quantity of chitosan suitable for planting a 64.75 hectare field (quarter section) of wheat would be mixed as follows: 1.089 kilograms of crab shell chitosan dissolved in 30.28 liters of 1% acetic acid. 48 hours is allowed at room temperature for the chitosan to dissolve with stirring. $H_2O$ is then added to bring the volume to 98.42 liters or until the viscosity is reduced enough to feed through the dispenser of commercial seed treating machinery. (Most seed treatment machines utilized to handle water based seed treatments can be utilized with the aqueous solution of chitosan.) The solution is neutralized to pH 6.0 to 6.5 with 0.757 to 0.871 liters of 6.0 N NaOH. NaOH is added slowly with stirring, because localized changes to a pH higher than 7.0 will cause the chitosan to precipitate. Once near neutrality, the viscosity of the opaque aqueous preparation of chitosan is reduced to the designed viscosity with $H_2O$ to approximately 98.42 liters. From this, approximately 0.473 liters is added to each bushel (27.22 kg.) of wheat seed. This volume of aqueous chitosan increases the moisture percentage of 27.22 kilograms of wheat seed by 1.6%.

Chitosan seed treatments were found to be effective using rates ranging from 60 $\mu g$ chitosan per gram of wheat seed to 1000 $\mu g$ chitosan per gram of wheat seed. Optimal results were obtained at 250 $\mu g$ chitosan per gram of wheat seed. This rate is 0.00635 kilogram chitosan per 27.22 kilograms (1 bushel) of wheat seed. 27.22 kilograms per 0.4047 hectare is the average seeding rate for wheat in most areas.

For barley, optional results are obtained at about 60 $\mu g$ per gram of barley seed. For oats, such results are obtained in the range 475 $\mu g$ to 525 $\mu g$ per gram of oats seed.

The native chitosan required to treat seed prior to planting is inexpensive. For winter wheat, chitosan treated wheat seed can be planted in late summer or as early as August as moisture is available. The chitosan treatment enhances stem diameter by approximately 10%. Although chitosan-treated plants grown in soils heavily infested with root rotting disease are susceptible to development of some rotting symptoms such as stem discoloration and white heads, the larger stem diameter and the extensive root system caused by the treatment maintain greater stem strength and an adequate water transporting capacity of stem vascular systems. As a result of seed treatment with this naturally occurring compound, 10-30% higher yields are obtained at a low cost, soil erosion is minimized, and the chitosan is readily degraded to simple amino sugar residues and/or metabolized by soil organisms.

Plants and micro-organisms contain chitosanase and other degradative enzymes with the potential to digest chitosan into smaller fragments and eventually into hexosamines that can be utilized as nutrients by soil microflora.

If seed is treated in a humid environment, a post-treatment drying step must be added to reduce the moisture content of the treated grain to the 10-14% range in order to prevent premature germination of the seed; therefore, the more viscous the chitosan preparation, the less drying that will be required. Highly viscous chitosan preparations can be mixed with seed using any machinery marketed for cement mixing. Modifications of grain augering devices will also enable chitosan to be added to seed as it is being loaded aboard trucks just prior to transport to the field for planting. This eliminates the need for extensive drying to prevent seed germination.

Chitosan seed applications are not detrimentally influenced by fertilizer supplements, herbicide applications or irrigation programs. Other commercial seed treatments, e.g., insecticides and fungicides, should be applied prior to chitosan. Components already on the seed will be attached to the seed by the chitosan, which leaves a "cellophane-like" surface on seed after drying. The chitosan-treated seed can be planted directly in any commercial planter. Special planters that automatically administer fertilizers, soil sterilants, herbicides, etc. can be utilized to treat seeds with chitosan as they are being planted. Chitosan labelled with tritium, [$^3$H]-Chitosan, added to seeds was translocated to the developing plant indicating that a large portion of the chemical is distributed systemically.

Dry chitosan can be stored indefinitely at room temperature without loss of biological activity. Chitosan can be mixed as described above at room temperature. Chitosan has no known toxicity and can be supplemental to the diet of animals without detrimental side effects. The physical irritation properties of chitosan have not been investigated in long term studies, however, and, therefore, the same basic precautions taken in the handling of other fibrous materials or powders, e.g., cotton fibers or flour, may apply to chitosan.

The root enhancing, stem diameter increasing, and strengthening effect of chitosan seed treatment is seen at both early and late seeding dates for winter crops; however, the major beneficial effects for erosion reduction are obtained with early seeding dates. This allows the development of the large seedling plants needed for ground cover prior to the onset of winter rains and snow melts while the chitosan minimizes the problem of root rotting.

The following data illustrate examples of enhanced properties obtained in wheat, oats, and barley through the use of this invention.

EXAMPLE 1. Enhanced Seedling Development

Seedlings from chitosan treated Daws wheat seed (200 $\mu g$ chitosan/g seed) 4 months after planting at Washtuchna, Wash. under circle irrigation, Oct. 15, 1983.

| Seed Treatment | Ave. diameter of crown (lower stem) mm | Ave. length of stem from crown to first leaf cm | Ave. wt. root system per 30 plants | |
|---|---|---|---|---|
| | | | fresh wt g | dry wt g |
| $H_2O$ control | 2.3 | 3.7 | 1.002 | .139 |
| Chitosan (200 $\mu g$/g seed) | 3.7 | 3.8 | 2.690 | .330 |

EXAMPLE 2. Reduced Lodging

Daws winter wheat 1983 crop lodging reading on outside row of 4'×100' plot.

| Treatment g chitosan/gram seed | Stems lodged no. |
|---|---|
| Chitosan 62 | 275 |
| Control | 468 |
| Chitosan 125 | 313 |
| Control | 948 |
| Chitosan 250 | 143 |
| Control | 835 |
| Chitosan 500 | 186 |
| Control | 652 |

| Treatment g chitosan/gram seed | Stems lodged no. |
|---|---|
| Chitosan 1000 | 250 |
| Control | 410 |

EXAMPLE 3. Increased Stem Diameter

Effect of chitosan seed treatment on stem diameter of Daws wheat at maturity—1983

| Chitosan applied per gram seed g | Stem diameter mm | % increase |
|---|---|---|
| Chitosan 62 | 3.872[a] | — |
| Control | 3.239 | 19 |
| Chitosan 125 | 3.432 | — |
| Control | 3.231 | 6 |
| Chitosan 250 | 3.606 | — |
| Control | 3.322 | 9 |
| Chitosan 500 | 3.997 | — |
| Control | 3.651 | 9 |

[a] Average diameter of 100 stems.

EXAMPLE 4. Enhanced Yield

Effect of Chitosan Seed Treatment on Daws Winter Wheat Yield in 1983

| | Application kg/bushel (27.2 kg) seed | Avg. yield kh/hectare | % Increase Over Control |
|---|---|---|---|
| Chitosan 1000 μg/g | .0268 | 6066.0[a] | 14% |
| Control | | 5299.3 | |
| Chitosan 500 μg/g | .0132 | 6032.3 | 13% |
| Control | | 5232.1 | |
| Chitosan 250 μg/g | .0064 | 6341.7 | 21% |
| Control | | 5662.5 | |
| Chitosan 125 μg/g | .0032 | 6153.4 | 8% |

[a] Yield was an average of four replications. Plot size was 1.22 m × 9.14 m. Lodging in control plots was up to 60%. Yield included lodged wheat recovered by hand at harvest.

EXAMPLE 5. Enhanced Yield

| Fielder spring wheat treatment yield - 1982 | % of control |
|---|---|
| Chitosan (320 μg/g) seed treatment only | 131 |
| Control | 100 |

EXAMPLE 6. Enhanced Yield

| Daws winter wheat treatment - 1982 yield | % of control |
|---|---|
| Chitosan (500 μg/g) seed treatment | 107 |
| Control | 100 |

EXAMPLE 7. Enhanced Disease Resistance

Effects of Chitosan Seed Treatment Daws Wheat Pseudocercosporella herpotrichoides Disease symptoms on Wheat Straw at Harvest

| Symptom Value | No. of Straws/Symptom Value Category (Chitosan treatment and control) | | | | |
|---|---|---|---|---|---|
| | 0 | 1 | 2 | 3 | 4 |
| 62 μg/g | 4 | 22 | 35 | 22 | 17 |
| Control | 8 | 28 | 40 | 24 | 8 |
| 125 μg/g | 5 | 13 | 24 | 12 | 46 |
| Control | 1 | 8 | 21 | 49 | 21 |
| 250 μg/g | 2 | 15 | 19 | 48 | 18 |
| Control | 0 | 8 | 39 | 48 | 5 |
| 500 μg/g | 7 | 19 | 37 | 21 | 16 |
| Control | 0 | 4 | 35 | 59 | 7 |
| 1000 μg/g | 0 | 8 | 32 | 55 | 5 |
| Control | 1 | 9 | 38 | 48 | 4 |

Mature Stem Symptom Values
Clean Straw = 0
Slight Discoloration = 1
Scattered Lesions = 2
Coalescing Lesions = 3
Diseased & Broekn = 4

EXAMPLE 8. Enhanced Yield

| KAMIAK BARLEY WINTER GROWN Whitlow Farm, Pullman, Washington | | |
|---|---|---|
| TREATMENT | kg/hectare | % OF CONTROL |
| Control[a] | 8135.20 | — |
| 1000 μg/g seed[b] | 7568.77 | 93 |
| 500 μg/g seed[b] | 8301.23 | 102 |
| 250 μg/g seed[b] | 8276.79 | 101 |
| 125 μg/g seed[b] | 8960.43 | 110 |
| 62 μg/g seed[b] | 10010.31 | 123 |

[a] Average of 10 plots (generally 1.22 m × 9.14 m); chitosan was applied with water — equivalent amount of water without the chitosan was applied to the control plots.
[b] Average of 2 plots (generally 1.22 m × 9.14 m).

EXAMPLE 9. Enhanced Yield

| CORRET OATS SPRING PLANTED Plant Pathology Farm, Pullman, Washington | | |
|---|---|---|
| TREATMENT | kg/hectare | % OF CONTROL |
| Control[a] | 2485.47 | — |
| 1000 μg/g seed[b] | 2734.57 | 110 |
| 500 μg/g seed[b] | 3344.90 | 135 |
| 250 μg/g seed[b] | 2758.95 | 111 |
| 125 μg/g seed[b] | 2392.72 | 96 |
| 62 μg/g seed[b] | 2148.56 | 86 |

[a] Average of 10 plots (generally 1.22 m × 9.14 m); chitosan was applied with water — an equivalent amount of water without the chitosan was applied to the control plots.
[b] Average of 2 plots (generally 1.22 m × 9.14 m).

EXAMPLE 10. Wheat Seedling Weights

| Variety: VONA Date harvested: 18 December 1985 Location: Alva, Oklahoma | | | | |
|---|---|---|---|---|
| | mean wt per stem (g) | | mean wt per root (g) | |
| | fresh | dry | fresh | dry |
| Group I | | | | |
| Control | 2.01 | 0.38 | 1.98 | 0.04 |
| Chitosan solution 0.473 liter | 3.13 | 0.47 | 2.87 | 0.01 |
| % of control | 156 | 124 | 145 | 25 |
| Group II | | | | |
| Control | 2.3 | 0.23 | 0.43 | 0.04 |
| Chitosan solution 0.473 liter | 2.4 | 0.24 | 0.33 | 0.05 |

-continued

| Variety: VONA |   |   |   |   |
|---|---|---|---|---|
| Date harvested: 18 December 1985 |   |   |   |   |
| Location: Alva, Oklahoma |   |   |   |   |
|  | mean wt per stem (g) | | mean wt per root (g) | |
|  | fresh | dry | fresh | dry |
| % of control | 104 | 104 | 77 | 125 |

EXAMPLE 11

Wheat Seedling Test Data Seedling Crown Diameter

| Variety: VONA |   |   |   |   |
|---|---|---|---|---|
| Planted: 1 November 1984 | | | | |
| Harvested: 5 January 1985 | | | | |
| Location: Alva, Oklahoma | | | | |
| Treatment | No. of samples | mean crown diameter (cm) | Statistical Deviation | % of control |
| Control | 15 | 5.347 | 1.147 | 100 |
| Chitosan 250 μg/g | 15 | 8.893 | 5.154 | 166 |

EXAMPLE 12.

| 1984-85 Vona Wheat Yield |   |   |   |   |
|---|---|---|---|---|
| Date of harvest: 5 June 1985 | | | | |
| Location: Alva, Okalhoma | | | | |
| Treatment | No. of plots | kg hectare | Statistical Deviation | % of control |
| control | 6 | 2858.1 | 5.6 | 100 |
| Chitosan 250 μg/g | 6 | 3355.8 | 5.9 | 117 |

EXAMPLE 13.

| 1983-84 TAM W-101 Wheat Yield |   |   |   |   |
|---|---|---|---|---|
| Date of harvest: 12 June 1984 | | | | |
| Location: Alva, Oklahoma | | | | |
| Treatment | No. of plots | kg hectare | Statistical Deviation | % of control |
| control | 6 | 3349.1 | 5.9 | 100 |
| Chitosan 250 μg/g | 6 | 3685.3 | 6.2 | 110 |

EXAMPLE 14.

| 1985 Comparison of Yield for Chitosan vs. Benlate |   |   |
|---|---|---|
| Location: Whitlow Farm, Pullman, Washington | | |
|  | Kg/hectare | % of control |
| I. Hill - 81 | | |
| H$_2$O Control[a] | 4794.9 | — |
| Benlate Treated[b] | 3651.7 | 76 |
| 1000 μg/g + Benlate[c] | 3396.1 | 71 |
| 500 μg/g + Benlate[c] | 3961.0 | 83 |
| 250 μg/g + Benlate[c] | 4041.7 | 84 |
| 125 μg/g + Benlate[c] | 4176.2 | 87 |
| 62 μg/g + Benlate[c] | 3254.9 | 68 |
| 1000 μg/g[c] | 4088.8 | 85 |
| 500 μg/g[c] | 4673.9 | 97 |
| 250 μg/g[c] | 5756.6 | 120 |
| 125 μg/g[c] | 5427.1 | 113 |
| 62 μg/g[c] | 4922.7 | 103 |
| II. Daws | | |
| H$_2$O Control[c] | 2757.3 | — |
| Benlate[c] | 1667.8 | 60 |
| 1000 μg/g + Benlate[c] | 1943.5 | 70 |
| 500 μg/g + Benlate[c] | 1049.1 | 38 |
| 250 μg/g + Benlate[c] | 1499.7 | 54 |
| 1000 μg/g[c] | 2710.2 | 98 |
| 500 μg/g[c] | 3961.0 | 144 |
| 250 μg/g[c] | 3799.6 | 138 |

[a]Averaged over 6 reps 3.048 m × 0.356 m.
[b]Averaged over 8 reps 3.048 m × 0.356 m.
[c]Averaged over 2 reps 3.048 m × 0.356 m.

EXAMPLE 15.

| 1982-83 Stephens Wheat Harvest Yield |   |   |
|---|---|---|
| Treatment | kg/hectare | % of control |
| H$_2$O Control[a] | 6536.7 | — |
| Chioosan 500 μg/g[b] | 7081.4 | 108 |
| Chitosan 250 μg/g[b] | 6691.4 | 102 |
| Chitosan 125 μg/g[b] | 6395.5 | 98 |
| Chitosan 62 μg/g[b] | 6247.5 | 96 |

[a]Average of 7.62 m × 1.22 m replications.
[b]Average of 7.62 m × 1.22 m replications.

EXAMPLE 16.

| 1984-85 Daws Wheat Harvest Yield |   |   |
|---|---|---|
| Location: Whitlow Farm, Pullman, Washington | | |
| Treatment | kg/hectare | % of Control |
| H$_2$O Control | 3214.6 | — |
| 1000 μg/g | 3712.2 | 115 |
| 500 μg/g | 4008.1 | 125 |
| 250 μg/g | 3880.3 | 121 |

EXAMPLE 17.

| 1984-85 Hill '81 Wheat Yield |   |   |
|---|---|---|
| Location: Whitlow Farm, Pullman, Washington | | |
| Treatment | kg/hectare | % of Control |
| H$_2$O Control[a] | 4129.2 | — |
| 1000 μg/g[b] | 3920.7 | 95 |
| 500 μg/g[b] | 4337.6 | 105 |
| 250 μg/g[b] | 4963.1 | 120 |
| 125 μg/g[b] | 4922.7 | 119 |
| 62 μg/g[b] | 4297.3 | 104 |

[a]Average of 50 3.048 m × 0.356 m replications.
[b]Average of 10 3.048 m × 0.356 m replications.

EXAMPLE 18.

| 1985 Corret Spring Oat Yield |   |   |
|---|---|---|
| Location: Whitlow Farm, Pullman, Washington | | |
| Treatment | kg/hectare | % of Control |
| H$_2$O Control[a] | 1001.6 | — |
| 500 μg/g[b] | 876.4 | 87 |
| 250 μg/g[b] | 793.0 | 79 |
| 125 μg/g[b] | 1544.2 | 154 |
| 62 μg/g[b] | 667.8 | 67 |

[a]Average of 35 3.048 m × 0.356 m replications.
[b]Average of 7 3.048 m × 0.356 m replications.

EXAMPLE 19.

1985-86 Boyer Barley Yield
Location: Soil Conservation Service Field Station
Pullman, Washington

| Treatment | No. of plots | kg hectare | % of control |
|---|---|---|---|
| H2O Control | 12 | 4718.6 | 100 |
| Chitosan solution 0.1183 liters/ 45.36 kg seed | 13 | 5884.2 | 125 |
| H2O control | 12 | 4920.3 | 100 |
| Chitosan solution 0.1479 liters/ 45.36 kg seed | 13 | 5839.4 | 119 |
| H2O Control | 10 | 4965.1 | 100 |
| Chitosan solution 0.1775 liters/ 45.36 kg seed | 11 | 7677.5 | 155 |
| H2O Control | 11 | 6881.7 | 100 |
| Chitosan solution 0.2366 liters/ 45.36 kg seed | 13 | 8013.7 | 116 |
| H2O Control | 12 | 6298.9 | 100 |
| Chitosan solution 0.2958 liters/ 45.36 kg seed | 13 | 7139.5 | 113 |

Plot size = 3.048 m × 0.357 m = 1.087 m$^2$.
Chitosan solution is 2% chitosan and 98% inert ingredients.

Having fully described the present invention, it will be apparent to those skilled in the art that modifications to the method described herein may be made without departing from the scope of the present invention. While the embodiments described involve wheat, oats, and barley the process is generally applicable to cereal crops. Only the wheat, oats, and barley embodiments have been included for the sake of brevity. Therefore, the scope of this invention is not intended to be limited except as may be required by the lawful scope of the following claims.

I claim:

1. A method of enhancing cereal crop yield, straw strength, stem diameter, and root development comprising:
applying chitosan in solution in an effective amount to cereal crop seed.

2. The method of claim 1 wherein said cereal crop is wheat.

3. The method of claim 1 or claim 2 wherein said chitosan is dissolved in a dilute aqueous acid to form a solution prior to application.

4. The method of claims 1 or 2 wherein the rate of application is between 60 $\mu$g/g seed and 1000 $\mu$g/g seed.

5. The method of claim 1 wherein said cereal crop is barley.

6. The method of claim 1 wherein said cereal crop is rye.

7. The method of claim 1 wherein said cereal crop is oats.

8. The method of claim 1 wherein said cereal crop is rice.

9. The method of claim 2 wherein the rate of application is between 225 $\mu$g/g wheat seed and 275 $\mu$g/g wheat seed.

10. The method of claim 5 wherein the rate of application is substantially 60 $\mu$g/g barley seed.

11. The method of claim 7 wherein the rate of application is between 475 $\mu$g/g oat seed and 525 $\mu$g/g oat seed.

12. The method of claim 3 wherein the rate of application is between 60 $\mu$g/g seed and 1000 $\mu$g/g seed.

* * * * *

UNITED STATES PATENT AND TRADEMARK OFFICE
CERTIFICATE OF CORRECTION

PATENT NO. : 4,978,381

DATED : December 18, 1990

INVENTOR(S) : Lee A. Hadwiger

It is certified that error appears in the above-identified patent and that said Letters Patent is hereby corrected as shown below:

Title page, item [*], change "Sep. 12, 2006" to --Dec. 12, 2006--.

Signed and Sealed this

Sixth Day of October, 1992

Attest:

DOUGLAS B. COMER

*Attesting Officer*   *Acting Commissioner of Patents and Trademarks*